United States Patent [19]

Dowell et al.

[11] Patent Number: 5,393,519
[45] Date of Patent: Feb. 28, 1995

[54] SHAMPOO COMPOSITIONS

[75] Inventors: Teresa J. Dowell, Downers Grove; Gerald P. Newell, Hoffman Estates; Eugene Zeffren, Lincolnshire, all of Ill.

[73] Assignee: Helene Curtis, Inc., Chicago, Ill.

[21] Appl. No.: 969,382

[22] Filed: Oct. 30, 1992

Related U.S. Application Data

[63] Continuation of Ser. No. 859,128, Mar. 27, 1992, abandoned.

[51] Int. Cl.$^6$ .......... A61K 7/06; C11D 3/48; C11D 9/50
[52] U.S. Cl. ............... 424/70.11; 252/106; 252/107; 514/880; 514/881; 424/70.12; 424/70.122; 424/70.14; 424/70.15; 424/70.24; 424/70.31
[58] Field of Search .......................... 424/70

[56] References Cited

U.S. PATENT DOCUMENTS

| | | | |
|---|---|---|---|
| 4,281,201 | 7/1981 | Abend | 564/506 |
| 4,472,375 | 9/1984 | Bolich, Jr. et al. | 424/70 |
| 4,548,810 | 10/1985 | Zofchak | 424/59 |
| 4,704,272 | 11/1987 | Oh et al. | 424/70 |
| 4,741,855 | 5/1988 | Grote et al. | 252/142 |
| 4,788,006 | 11/1988 | Bolich, Jr. et al. | 252/550 |
| 4,902,499 | 2/1990 | Bolich, Jr. et al. | 424/70 |
| 4,960,588 | 10/1990 | Hoshowski et al. | 424/71 |

FOREIGN PATENT DOCUMENTS

| | | | |
|---|---|---|---|
| 1003345 | 9/1965 | United Kingdom . | |
| WO88/03016 | 5/1988 | WIPO | A61K 7/06 |
| WO92/00283 | 1/1992 | WIPO | A61K 7/00 |

*Primary Examiner*—Dale R. Ore
*Attorney, Agent, or Firm*—Marshall, O'Toole, Gerstein, Murray & Borun

[57] ABSTRACT

A hair shampoo composition comprising a cleansing surfactant; a water-insoluble hair treating compound, like a hair conditioner or an antidandruff agent; a suspending agent comprising an amine including at least one long carbon chain and a suitable acid; and a suitable carrier, and a method of treating hair are disclosed. The shampoo compositions effectively suspend the water-insoluble hair-treating compound, effectively cleanse the hair and effectively deliver the water-insoluble hair-treating compound to the hair or scalp.

24 Claims, No Drawings

SHAMPOO COMPOSITIONS

CROSS REFERENCE TO A RELATED APPLICATION

This application is a continuation of application Ser. No. 07/859,128, filed Mar. 27, 1992, now abandoned.

FIELD OF THE INVENTION

The present invention is directed to a shampoo composition including a new and improved suspending agent and to a method of treating hair, wherein the aqueous shampoo composition includes a water-insoluble hair treating compound, such as a silicone conditioning agent or a particulate antidandruff agent, and effectively resists phase separation. More particularly, a shampoo composition of the present invention is an unexpectedly stable suspension for the improved topical delivery of a water-insoluble hair treating compound from an aqueous shampoo composition to the hair or scalp. Therefore, in general, the present invention is directed to a shampoo composition comprising: (a) a cleansing surfactant, such as an anionic surfactant, like sodium lauryl sulfate or ammonium lauryl ether sulfate; (b) a water-insoluble hair treating compound, such as a hair conditioner, like a polydimethylsiloxane, or an antidandruff agent, like zinc pyrithione; (c) a suspending agent comprising: (i) a water-insoluble amine having the general structural formula (I) or (II) or (III), wherein $R_1$ is an alkyl group, straight chain or branched, including

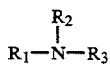 (I)

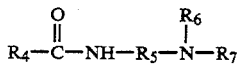 (II)

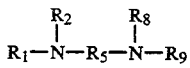 (III)

at least about 16 carbon atoms; $R_2$ and $R_3$ are, independently, selected from the group consisting of hydrogen, an alkyl group including one to about 22 carbon atoms, benzyl and phenyl; $R_4$ is an alkyl group, straight chain or branched, including at least 13 carbon atoms; $R_5$ is an alkylene moiety including 1 to 4 carbon atoms; $R_6$ and $R_7$ are, independently, alkyl groups including 1 to 4 carbon atoms; and $R_8$ and $R_9$ are, independently, hydrogen or an alkyl group including 1 to 4 carbon atoms, and (ii) a suitable acid selected from the group consisting of an inorganic mineral acid, an aliphatic carboxylic acid including up to about 22 carbon atoms, an aromatic carboxylic acid, and combinations thereof; and (d) a suitable carrier comprising water; wherein the composition includes a sufficient amount of acid such that essentially no solid particles of the amine of general structural formula (I) or (II) or (III) are present in the composition. The shampoo composition effectively resists phase separation, and effectively delivers the water-insoluble hair treating compound to the hair or scalp.

BACKGROUND OF THE INVENTION

Most individuals buy and use a hair shampoo for its cleansing properties. A consumer often also desires a hair shampoo that imparts other desirable properties to the hair or scalp, such as conditioning, antidandruff and set retention properties. For example, consumers often desire sufficiently-conditioned hair that holds a preset configuration. However, hair shampoos generally are formulated with highly effective synthetic surfactants, like anionic surfactants, that primarily cleanse as opposed to conditioning the hair. Therefore, shampoos usually neither aid in the detangling of wet hair nor impart any residual conditioning benefits to dry hair, such as manageability or styleability of hair sets.

The hair normally is left in an unconditioned, cosmetically-unsatisfactory state after washing with an anionic surfactant-based hair shampoo, because anionic surfactants not only remove the dirt and soil from the hair, but also remove essentially all of the sebum naturally present on the surface of the hair fibers. Therefore, although anionic surfactants effectively cleanse the hair, the anionic surfactants also leave the hair in a cosmetically-unsatisfactory condition. In general, hair shampoo compositions containing anionic surfactants, or nonionic surfactants or amphoteric surfactants, leave the hair with an undesirable harsh, dull and dry touch, or feel, usually called "creak", after the hair is shampooed and then rinsed with water.

Thoroughly cleansed hair also is extremely difficult to comb, in either the wet or the dry state, because the individual hair fibers tend to snarl, kink and interlock with each other. In addition, incompletely dried hair, such as hair dried with towel, has poor brushing properties, and after complete drying, the hair does not set well. Furthermore, the combing or brushing property of the hair remains, poor, and the hair has undesirable electrostatic properties in a low humidity atmosphere that causes the hair to "fly away", thereby further reducing the brushing properties of the hair. The unsatisfactory combing or brushing property of hair immediately after shampooing, also causes hair damage, such as split ends or hair breakage. In addition, the natural luster and resiliency of the hair is reduced. Consequently, the overall unsatisfactory condition of the shampooed hair usually necessitates a subsequent post-shampoo treatment of the hair with a conditioning composition to improve these undesirable physical characteristics. These conditioning compositions normally are applied separately from the hair shampoo, and usually are rinses or cream-like lotions containing a cationic compound that is substantive to the hair.

Therefore, consumer needs traditionally have been met by the application of a shampoo to cleanse the hair, followed by the application of a conditioner composition to improve wet combing and other properties. The commonly accepted method has been to shampoo the hair, followed by rinsing the hair, and then separately applying a conditioner composition, followed by a second rinse. As previously discussed, freshly shampooed hair is inclined to knot and tangle, and therefore is difficult to comb and difficult to manage. The wet combing problem has been solved by treating shampooed hair with a conditioner composition that coats the hair shaft and causes the individual hair shafts in a tress to resist tangling and matting because of the conditioner residue retained on the shaft.

Consumers also often use an antidandruff shampoo. The incorporation of antidandruff agents into anionic surfactant-based hair shampoos is well known. The antidandruff agents not only must relieve the flaking and itching symptoms of dandruff, but also must be substantive to the skin and hair in order to extend the efficacy of the antidandruff agent from one shampoo treatment to the next. These properties are most often found in compounds that are insoluble in aqueous media, and this inherent insolubility of the antidandruff agent makes formulation of a stable, aqueous, anionic surfactant-based antidandruff shampoo a difficult problem.

In order to incorporate effective, water-insoluble antidandruff agents into an aqueous surfactant-based hair shampoo, one or more suspending agents are required to maintain the antidandruff agent homogeneously dispersed throughout the aqueous solution. Failure to adequately suspend the antidandruff agent leads to eventual shampoo separation as the antidandruff agent settles to the bottom of the container, and results in poor dandruff control and consumer complaints. As a result, investigators have continuously sought suitable suspending agents capable of effectively dispersing antidandruff agents, such as zinc pyrithione or sulfur, in aqueous media.

While numerous shampoos that include hair conditioners or antidandruff compounds have been disclosed, such shampoos have not been totally satisfactory for a variety of reasons. In regard to shampoo-conditioner compositions, one problem relates to compatibility problems between anionic cleansing surfactants and cationic compounds that are good conditioning agents. This compatibility problem has caused workers in the field to investigate other surfactants, such as nonionics, amphoterics and zwitterionics, as a total or partial replacement for the anionic cleansing surfactant. Many of these efforts are reflected in patents issued in the shampoo conditioner area. See for example U.S. Pat. No. 3,849,348 to Hewitt; U.S. Pat. No. 3,990,991 to Gerstein; and U.S. Pat. No. 3,822,312 to Sato. However, the nonionic, amphoteric and zwitterionic surfactants are inferior cleansing surfactants compared to the anionic surfactants.

Accordingly, to avoid the cationic-anionic incompatibility problem, to increase the degree of conditioning imparted to the hair and to maintain the cleansing efficiency of the hair shampoo, investigators incorporated silicone compounds into surfactant-based shampoo compositions. A problem inherent in formulating a silicone-based shampoo conditioner is the phase separation that results when a water-insoluble silicone conditioning agent is included in the aqueous shampoo-conditioner composition. Silicones included in shampoo-conditioner compositions have been disclosed in a number of different patents, including U.S. Pat. No. 2,826,551 to Green; U.S. Pat. No. 3,964,500 to Drakoff; U.S. Pat. No. 4,364,837 to Pader; British Pat. No. 849,433 to Woolston; U.S. Pat. No. 4,741,855 to Grote, et al.; U.S. Pat. Nos. 4,788,006 and 4,902,499 to Bolich, Jr. et al. and U.S. Pat. No. 4,704,272 to Oh et al.

A particularly difficult problem encountered in silicone-containing shampoo-conditioners is maintaining a dispersed, insoluble silicone material suspended in stable form, while retaining the cleansing and conditioning performance of the conditioning shampoo-conditioner product. A variety of materials have been proposed for inclusion in silicone-containing conditioning shampoos for purposes of thickening and stabilization such as xanthan gum, long chain acyl derivatives, long chain amide oxides, and long chain alkanolamides as disclosed in U.S. Pat. Nos. 4,788,006; 4,704,272; and 4,741,855.

In particular, Oh et al., in U.S. Pat. No. 4,704,272, disclose shampoo compositions including an anionic surfactant, a nonvolatile silicone, a hair conditioning agent and a suspending agent. The hair conditioning agent can be a tri-long chain ($C_8$–$C_{22}$) amine, such as tri(isodecyl)amine or tri-$C_{13}$ amine. Oh et al. also teach that a suspending agent, like a xanthan gum or a long chain acyl derivative, is essential to the composition. Surprisingly, it has been found that a primary, secondary or tertiary amine including at least one carbon chain having at least 16 carbon atoms, and neutralized with a suitable acid, provides a stable shampoo composition that effectively resists separation of the water-insoluble hair-treating compound from the shampoo composition without the need for a separate suspending agent.

Bolich et al., in U.S. Pat. No. 4,472,375, disclose an aqueous hair conditioning composition comprising a volatile hydrocarbon or a volatile silicone; a nonionic thickening agent; a quaternary ammonium salt and/or a salt of a fatty amine. The composition of Bolich et al. does not include an anionic cleansing surfactant and relies upon the nonionic thickening agent, e.g., a polymer, to suspend the water-insoluble ingredients. The present composition does not rely on a thickening agent to maintain phase stability of the composition.

A similar problem is encountered in regard to an antidandruff shampoo wherein a water-insoluble particulate antidandruff agent tends to separate from the aqueous hair shampoo base. Therefore, compositions containing insoluble particulate matter, like an antidandruff agent, require a suspending agent to assist in dispersing the particulate matter evenly throughout the composition. The suspending agent can be any one of a number of inorganic minerals or synthetic or natural polymers or gums. Among the most often used suspending agents are colloidal aluminum oxide, modified magnesium aluminum silicate, xanthan gum, fumed silica, algin products, polyacrylic acid, sodium carboxymethylcellulose, hydroxypropylcellulose, synthetic sodium magnesium silicate, colloidal attapulgite clay, lignins and alkanolamides. Any antidandruff agent and additional suspending agents added to a basic hair shampoo base should add antidandruff properties to the shampoo without detracting from the cleansing efficiency and esthetic appeal of the shampoo. Unfortunately, the antidandruff agents and necessary suspending agents often adversely affect the foaming characteristics of the shampoo composition.

Therefore, the need for improved stable compositions that condition the hair, i.e., render the hair more manageable, or that impart antidandruff properties, has long been recognized in the art. Consequently, the present invention is directed to stable hair shampoo compositions including a cleansing surfactant and a water-insoluble hair treating compound, like a silicone conditioner or an antidandruff agent, wherein the hair shampoo composition effectively resists phase separation because of the presence of a new suspending agent comprising an amine including at least one alkyl chain of sufficient chain length and a suitable acid.

As will be demonstrated more fully hereinafter, a hair shampoo composition, comprising a cleansing surfactant; a water-insoluble hair treating compound, like a silicone conditioning compound or an antidandruff agent; a suspending agent comprising a fatty amine having at least one alkyl group including at least about 16 carbon atoms or a fatty amidoamine having an alkyl group including at least about 13 carbon atoms and a suitable acid; and a suitable carrier, comprising water, effectively resists phase separation and effectively delivers the water-insoluble hair treating compound to the hair or scalp.

SUMMARY OF THE INVENTION

In brief, the present invention relates to a composition and method of shampooing and treating hair. More particularly, the present invention relates to a method of shampooing and treating the hair by contacting the hair with a composition comprising: (a) a cleansing surfactant; (b) a water-insoluble hair treating compound, such as a hair conditioner, like a polydimethylsiloxane, or an antidandruff agent, like zinc pyrithione; (c) a suspending agent comprising: (i) a water-insoluble amine having the general structural formula (I) or (II) or (III), wherein $R_1$ is an alkyl group, straight chain or branched, including

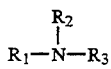   (I)

   (II)

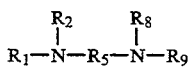   (III)

at least 16 carbon atoms; $R_2$ and $R_3$ are, independently, selected from the group consisting of hydrogen, an alkyl group including one to about 22 carbon atoms, benzyl and phenyl; $R_4$ is an alkyl group, straight chain or branched, including at least 13 carbon atoms; $R_5$ is an alkylene moiety including 1 to 4 carbon atoms; $R_6$ and $R_7$ are, independently, alkyl groups including 1 to 4 carbon atoms; and $R_8$ and $R_9$ are, independently, hydrogen or an alkyl group including 1 to 4 carbon atoms, and (ii) a suitable acid selected from the group consisting of an inorganic mineral acid, an aliphatic carboxylic acid including up to about 22 carbon atoms, an aromatic carboxylic acid and combinations thereof; and (d) a suitable carrier comprising water; wherein the composition includes a sufficient amount of acid such that essentially no solid particles of the amine of general structural formula (I) or (II) or (III) are present in the composition. An aqueous hair shampoo composition of the present invention effectively resists phase separation, demonstrates extended product stability, exhibits excellent cleansing properties and effectively delivers the water-insoluble hair treating compound to the hair or scalp to impart conditioning properties or antidandruff properties.

Therefore, one important aspect of the present invention is to provide a shampoo composition that cleanses the hair and imparts improved physical properties and cosmetic properties to the hair or scalp in a single application.

Another aspect of the present invention is to provide a physically stable, aqueous shampoo composition including a cleansing surfactant; a water-insoluble hair treating compound, like a silicone conditioner or an antidandruff agent; an amine including at least one alkyl group having a chain length of at least 16 carbon atoms or an amidoamine including an alkyl group having a chain length of at least 13 carbon atoms; and a suitable acid.

Another aspect of the present invention is to provide a new and improved shampoo, including a cleansing surfactant, such as a long chain alkyl sulfate or a long chain alkyl ether sulfate, and a water-insoluble hair treating compound, like a silicone conditioning agent or a particulate antidandruff agent, that is unexpectedly stable due to a new and improved suspending agent comprising an amine including at least one alkyl group having at least 16 carbon atoms or an amidoamine including an alkyl group having a chain length of at least 13 carbon atoms, or a combination thereof, and a suitable acid.

Still another aspect of the present invention is to provide a new and improved shampoo composition including about 3% to about 40% of a cleansing surfactant; about 0.1% to about 10% of a water-insoluble hair treating compound, such as a silicone conditioning compound or an antidandruff agent; wherein the water-insoluble hair treating compound is suspended in the shampoo composition by a suspending agent, the suspending agent comprising: (i) from about 1% to about 10% by weight of the composition of an amine having the general structural formula (I) or (II) or (III), wherein $R_1$ is an alkyl group, straight chain or branched, including at least 16 carbon atoms; $R_2$ and $R_3$ are, independently, selected from the group consisting

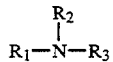   (I)

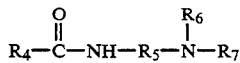   (II)

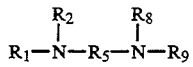   (III)

of hydrogen, an alkyl group including one to about 22 carbon atoms, benzyl and phenyl; $R_4$ is an alkyl group, straight chain or branched, including at least 13 carbon atoms; $R_5$ is an alkylene group including 1 to 4 carbon atoms; $R_6$ and $R_7$ are, independently, hydrogen or an alkyl group including 1 to 4 carbon atoms, and $R_8$ and $R_9$ are, independently, hydrogen or an alkyl group including 1 to 4 carbon atoms, and (ii) from about 0.05% to about 5% by weight of the composition of an inorganic mineral acid, an aliphatic carboxylic acid including up to about 22 carbon atoms, an aromatic carboxylic acid, or a combination thereof; wherein the composition includes a sufficient amount of acid such that essentially no solid particles of the amine of general structural formula (I) or (II) or (III) are present in the composition.

Another aspect of the present invention is to provide a stable shampoo composition that is capable of cleansing the hair and of imparting improved physical and cosmetic properties to the hair or scalp at a pH of about 3 to about 8.

Another aspect of the present invention is to provide a method of shampooing and treating hair by contacting the hair with a composition having a pH of about 3 to about 8, and comprising a cleansing surfactant; a water-insoluble hair treating compound, like a polydimethylsiloxane conditioning compound or an antidandruff agent; an amine having at least one carbon chain of at least 16 carbon atoms, an amidoamine having a carbon chain of at least 13 carbon atoms or a combination thereof; an inorganic mineral acid, an aliphatic carboxylic acid including up to about 22 carbon atoms, an aromatic carboxylic acid, or a combination thereof; and water.

The above and other aspects and advantages of the present invention will become apparent from the following detailed description of the preferred embodiments.

DETAILED DESCRIPTION OF THE PREFERRED EMBODIMENTS

A hair shampoo composition of the present invention comprises a cleansing surfactant, a water-insoluble hair treating compound, a suspending agent comprising a suitable amine, or a suitable amidoamine, and a suitable acid, and a carrier comprising water. The water-insoluble hair treating compound can be, for example, a water-insoluble hair conditioning compound, like a silicone or a hydrocarbon conditioning agent, or an antidandruff agent. In accordance with an important feature of the present invention, the amine of the suspending agent is a solid, water-insoluble amine having the general structural formula (I) or (II) or (III):

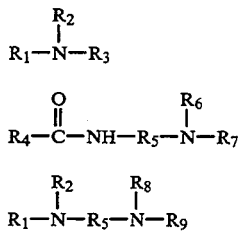

wherein $R_1$ is an alkyl group, straight chain or branched, including at least 16 carbon atoms; $R_2$ and $R_3$ are, independently, selected from the group consisting of hydrogen, an alkyl group including one to about 22 carbon atoms, benzyl and phenyl; $R_4$ is an alkyl group, straight chain or branched, including at least 13 carbon atoms; $R_5$ is an alkylene moiety including 1 to about 4 carbon atoms; $R_6$ and $R_7$ are, independently, an alkyl group including 1 to 4 carbon atoms; and $R_8$ and $R_9$ are, independently, hydrogen or an alkyl group including 1 to 4 carbon atoms. In accordance with an other important feature of the present invention, the acid of the suspending agent is selected from the group consisting of an inorganic mineral acid, an aliphatic carboxylic acid including up to about 22 carbon atoms, an aromatic carboxylic acid, and combinations thereof. The aqueous shampoo composition effectively resists phase separation, effectively cleanses the hair and effectively delivers the water-insoluble hair treating compound to the hair or scalp to impart conditioning properties, antidandruff properties or other desired hair or scalp properties.

The cleansing surfactant used in the composition and method of the present invention includes any of the anionic surfactants known or previously used in the art of hair shampoos. An anionic surfactant is the preferred cleansing surfactant in the composition of the present invention because it effectively cleanses the hair and generates a high, stable, foam level that consumers equate with cleaning efficiency. Nonionic surfactants generally are not as effective in cleansing the hair and do not provide the high foam level desired by consumers, but such surfactants impart mildness to the composition. Nonionic surfactants also can be included in a composition of the present invention to help increase and stabilize foam, to provide a suitable viscosity, or to furnish other functional or esthetic properties to the composition. Therefore, nonionic surfactants are not used as the primary cleansing surfactant in a composition of the present invention, but can be included in conjunction with an anionic cleansing surfactant.

Usually, the preferred anionic surfactant includes a hydrophobic moiety, such as a carbon chain including from about 8 carbon atoms to about 30 carbon atoms, and particularly from about 12 carbon atoms to about 20 carbon atoms; and further includes a hydrophilic moiety, such as sulfate, sulfonate, carbonate, phosphate or carboxylate. Often, the hydrophobic carbon chain is etherified, such as with ethylene oxide or propylene oxide, to impart a particular physical property, such as increased water solubility or reduced surface tension, to the anionic cleansing surfactant.

The anionic surfactants are well-known and have been widely used in the art of hair shampoos. Therefore, suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkyloxy alkane sulfonates, alkyl arylsulfonates, alkyl carbonates, alkyl ether carboxylates, fatty acids, sulfosuccinates, sarcosinates, octoxynol phosphates, nonoxynol phosphates, taurates, fatty taurides, sulfated monoglycerides, fatty acid amino polyoxyethylene sulfates and isothienates; or combinations thereof. Many additional anionic surfactants are described in McCUTCHEON'S, DETERGENTS AND EMULSIFIERS, 1989 ANNUAL, published by McCutcheon Division, MC Publishing Co., and incorporated herein by reference.

Usually, the anionic surfactant is present in the composition as a neutralized salt in the form of a sodium, potassium, lithium, ammonium, alkylammonium or hydroxyalkylammonium salt, wherein the alkyl moiety includes 1 to about 3 carbon atoms. The alkyl sulfates and alkyl ether sulfates are particularly effective classes of anionic surfactants. Exemplary anionic surfactants useful in the composition and method of the present invention include, but are not limited to, the ammonium, monoethanolamine, diethanolamine, triethanolamine, isopropylamine, sodium, potassium, lithium or magnesium salt of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide; or combinations thereof. An example of an especially useful anionic surfactant is a combination of a lauryl sulfate salt and a lauryl ether sulfate salt.

In conjunction with the anionic surfactant, an amphoteric surfactant can be included in the shampoo composition. An amphoteric surfactant enhances skin mildness and composition esthetics to improve consumer acceptance. Suitable classes of amphoteric surfactants included in the present invention include, but are not limited to, betaines, hydroxypropylsultaines, amine oxides and combinations thereof. Examples of specific amphoteric surfactants include, but are not limited to, cocamidopropyl betaine, lauramidopropyl betaine, coco/oleamidopropyl betaine, coco betaine, oleyl betaine, cocamidopropyl hydroxysultaine, tallowamidopropyl hydroxysultaine and dihydroxyethyl tallow glycinate or combinations thereof. In general, however, any amphoteric surfactant known and used in the art of hair shampoos can be included in the composition of the present invention.

The shampoo compositions of the present invention also can include a nonionic surfactant in combination with the anionic surfactant. In general, nonionic surfactants impart esthetic, physical or cleansing properties to the shampoo composition. Representative nonionic surfactants that can be included in a shampoo composition of the present invention include ethers of polyols and sugars; fatty acid alkanolamides; polyethylene glycols; the ethoxylated or propoxylated alkylphenols; ethoxylated or propoxylated fatty alcohols; and the condensation products of ethylene oxide with long chain amides. These nonionic surfactants, as well as numerous others not cited herein, are well known to person skilled in the art and are fully described in the literature, such as McCUTCHEON'S, DETERGENTS AND EMULSIFIERS, 1989 Annual, published by McCutcheon Division, MC Publishing Co.

In particular, a nonionic alkanolamide can be included in the composition to improve composition thickening and foam stability. Suitable alkanolamides include, but are not limited to, those known in the art of hair care formulations, such as cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA and combinations thereof.

In accordance with an important feature of the present invention, the anionic surfactant is present in the composition in an amount of about 3% to about 40%, and preferably about 5% to about 30%, by weight of the composition. It has been found that if the cleansing surfactant is present in an amount of less than 3% by weight of the composition, then the hair is not sufficiently cleansed when contacted with a shampoo composition of the present invention. Therefore, the cleansing surfactant, or combination of cleansing surfactants, generally is included in the hair shampoo composition of the present invention in a preferred amount ranging from about 5% to about 30% by weight of the composition, and to achieve the full advantage of the present invention, from about 10% to about 25% by weight of the composition. Furthermore, surprisingly and unexpectedly, even when a low amount of cleansing surfactant is included in the composition, such as from about 3% to about 10% by weight of the composition, the presence of the water-insoluble hair treating compound and the amine of the suspending agent do not adversely affect the generation of a sufficient and stable foam level for consumer acceptance.

In accordance with another important feature of the present invention, the hair shampoo composition includes a water-insoluble hair treating compound that imparts conditioning properties to the hair, imparts antidandruff properties to the hair and scalp or imparts other desired properties to the hair or scalp. Other classes of water-insoluble hair treating compounds, in addition to hair conditioners and antidandruff agents, that are useful in the shampoo composition of the present invention include, but are not limited to, hair colorants, hair fixatives and pearlizing agents. In general, the hair shampoo composition of the present invention includes from about 0.1% to about 10%, and preferably from about 0.5% to about 5% of the water-insoluble hair treating compound.

In one important embodiment of the present invention, the shampoo composition is a shampoo-conditioner wherein the water-insoluble hair treating compound is a silicone conditioning agent, a hydrocarbon conditioning agent, a water-insoluble fatty alcohol including about 12 to about 22 carbon atoms or a water-insoluble fatty ester including about 9 to about 34 carbon atoms, or other water-insoluble conditioning agent. In particular, the silicone conditioning agent can be a polyalkyl siloxane, a polyaryl siloxane or a polyalkylaryl siloxane. Mixtures of these silicone conditioning agents also can be used.

In one embodiment, the silicone conditioning agent is a nonvolatile silicone conditioning agent, like a polydimethylsiloxane compound, such as a mixture, in about a 2:1 weight ratio, of a low molecular weight polydimethylsiloxane fluid and a higher molecular weight polydimethylsiloxane gum. Preferred silicone gums include linear and branched polydimethylsiloxanes of the following general formula:

$(CH_3)_3SiO-[Si(CH_3)_2O]_n-Si(CH_3)_3$, wherein n is a number from 2,000 to about 15,000, and preferably from about 2,000 to about 7,000. Silicone gums useful in compositions of the present invention are available from numerous commercial sources, including General Electric Company, Waterford, N.Y., and Dow Corning Corp., Midland, Mich.

The nonvolatile polydimethylsiloxane agent is added to the composition of the present invention in an amount sufficient to impart improved combing and improved feel, such as softness, to the hair after shampooing. As referred to herein, the nonvolatile polydimethylsiloxane compounds are nonfunctional siloxanes having a viscosity of from about 5 to about 600,000 cs (centistoke), and preferably from about 350 to about 10,000 cs, at 25° C. The so-called "rigid silicones", as described in U.S. Pat. No. 4,902,499, incorporated herein by reference, having a viscosity above 600,000 cs at 20° C, e.g., 700,000 cs plus, and a weight average molecular weight of at least about 500,000 also are useful in accordance with the present invention.

A volatile silicone conditioning agent also is useful in the hair shampoo composition of the present invention as the water-insoluble hair treating compound, either alone or in conjunction with other water-insoluble hair treating compounds. The volatile silicone normally is a low molecular weight polydimethylsiloxane, however a low molecular weight polydimethylsiloxane including phenyl substituents also is useful in the compositions of the present invention. Furthermore, the low molecular weight polydimethylsiloxane compound can be a linear or a cyclic polydimethylsiloxane compound. The volatile polydimethylsiloxane compound provides lubrication and imparts hair conditioning properties to wet hair, and has sufficient volatility to slowly volatilize from the hair such that a residual buildup of silicone compound is not present on dry hair.

An example of a linear, low molecular weight, volatile polydimethylsiloxane compound useful in the composition and method of the present invention is hexamethyldisiloxane, available commercially under the tradename DOW CORNING 200 FLUID, from Dow Corning Corp., Midland, Mich. Hexamethyldisiloxane has a viscosity of 0.65 cs (centistokes), is highly volatile, is nongreasy, provides lubrication, and improves the overall combing properties of the hair. Other linear polydimethylsiloxanes, such as decamethyltetrasiloxane, having a boiling point of about 195° C. and a viscosity of 1.5 centistokes; octamethyltrisiloxane; and dodecamethylpentasiloxane, also are useful in the composition of the present invention.

In addition, the cyclic, low molecular weight, volatile polydimethylsiloxanes, having the Cosmetic, Toiletry and Fragrance Associate (CTFA) designation cyclomethicones, also are useful in the composition and method of the present invention. The cyclomethicones are low molecular weight, water-insoluble cyclic compounds having an average of about 3 to about 6 —[O—Si(CH$_3$)$_2$]— repeating group units per molecule and boil at atmospheric pressure in a range of from about 150° C. to about 250° C. Suitable cyclomethicones are available commercially under the tradenames SILICONE SF-1173 (octamethylcyclotetrasiloxane) and SILICONE SF-1202 (decamethylcyclopentasiloxane) from General Electric, Waterford, N.Y., and SILICONE 334 FLUID and SILICONE 345 FLUID from Dow Corning Corporation, Midland, Mich., the tetramer being listed first in each instance. The volatile cyclic silicones can be used in combination with a linear volatile silicone, and the volatile silicone conditioner can be used in conjunction with the nonvolatile silicone conditioner.

Another suitable water-insoluble conditioning compound that can be included in the composition of the present invention is a nonvolatile hydrocarbon, such as mineral oil. The nonvolatile hydrocarbons provide many of the same benefits as the silicone conditioning agents, and can be included in the composition in conjunction with a silicone conditioning agent.

In addition to nonvolatile hydrocarbon conditioning compounds, a volatile hydrocarbon conditioning compound can be included in the composition as the water-insoluble hair treating compound, either alone or in conjunction with other water-insoluble hair treating compounds. The volatile hydrocarbon conditioner, such as a hydrocarbon including about 10 carbon atoms to about 26 carbon atoms, has sufficient volatility to slowly volatilize from the hair to preclude a residual buildup of hydrocarbon on dry hair. The volatile hydrocarbon provides essentially the same benefits as the volatile silicone, such as lubrication and wet hair conditioning.

The preferred volatile hydrocarbon compound is an aliphatic hydrocarbon including from about 12 to about 24 carbon atoms, and has a boiling point in the range of from about 100° C. to about 300° C. Exemplary volatile hydrocarbons are depicted in general structural formula (IV), wherein n ranges from 2 to 5.

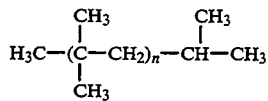  (IV)

Examples of volatile hydrocarbons useful in the compositions of the present invention are the commercially-available compounds PERMETHYL 99A and PERMETHYL 101A, corresponding to compound of general structural formula (IV) wherein n is 2 and 3, respectively, from Permethyl Corporation, Frazer, Pa. A volatile hydrocarbon compound is useful in the hair-conditioning composition of the present invention either alone, in combination with another volatile or nonvolatile hydrocarbon, or in combination with a volatile or nonvolatile silicone.

In another embodiment, the water-insoluble conditioning compound is a fatty alcohol, wherein the fatty alcohol includes about 12 to about 22 carbon atoms. Exemplary fatty alcohols include, but are not limited to, lauryl alcohol, oleyl alcohol, myristyl alcohol, tallow alcohol, cetyl alcohol, stearyl alcohol, cetearyl alcohol, behenyl alcohol and combinations thereof. A fatty alcohol can be used alone, or in combination with a silicone conditioning agent or a hydrocarbon conditioning agent.

In another embodiment, the water-insoluble conditioning compound is a fatty ester including about 9 to about 34 carbon atoms. The fatty component of the fatty ester can be derived from a fatty acid or a fatty alcohol, or a combination thereof. In addition, the fatty ester can be a straight chain fatty ester, like isopropyl myristate; a branched chain fatty ester, like Purcellin Oil; a benzoate ester, like $C_{12-15}$ alcohols benzoate; or a combination thereof.

For example, a useful class of fatty esters is derived from carboxylic acids having about 6 to about 12 carbon atoms, including both branched and straight chain carboxylic acids. In general, the $C_6$ to $C_{12}$ carboxylic acid is esterified with a fatty alcohol including about 12 to about 22 carbon atoms to provide a fatty ($C_{12}$ to $C_{22}$) ester of a $C_6$ to $C_{12}$ carboxylic acid that is useful in the present invention. Such fatty alcohols include, but are not limited to, lauryl alcohol, myristyl alcohol, cetyl alcohol, cetearyl alcohol, stearyl alcohol, isostearyl alcohol, oleyl alcohol, tallow alcohol, behenyl alcohol and mixtures thereof. Accordingly, fatty ($C_{12}$ to $C_{22}$) esters of $C_6$ to $C_{12}$ carboxylic acids useful in the composition and method of the present invention include, but are not limited to, cetyl octanoate, stearyl heptanoate, stearyl caprylate, stearyl octanoate, lauryl octanoate, myristyl heptanoate, and oleyl octanoate, or mixtures thereof. These fatty esters can occur naturally or can be synthesized.

In place of, or in combination with, the fatty ($C_{12}$ to $C_{22}$) ester of a $C_6$ to $C_{12}$ carboxylic acid, a fatty ester derived from a fatty acid including about 8 to about 22 carbon atoms esterified with an alcohol including 1 to about 6 carbon atoms can be included in the composition of the present invention. Examples of such fatty esters include, but are not limited to, isopropyl myristate, isopropyl palmitate, isopropyl laurate, isopropyl linoleate, isopropyl tallowate, isopropyl ricinoleate, methyl laurate, methyl linoleate, methyl myristate, methyl stearate, methyl ricinoleate, methyl carprylate, methyl oleate, methyl palmitate, methyl stearate, methyl behenate, methyl soyate, methyl tallowate, isopropyl behenate, isopropyl soyate, propyl oleate, butyl oleate, butyl stearate, methyl cocohate, methyl lardate, isobutyl palmitate, butyl myristate, ethyl palmitate, ethyl myristate, ethyl oleate, ethyl stearate, isobutyl stearate, isobutyl myristate and combinations thereof.

Another class of fatty esters that can be included in the composition of the present invention, either alone or in combination with the fatty esters described above, is the benzoate esters. Suitable benzoate esters include esters of benzoic acid wherein the esterifying alcohol includes about 8 carbon atoms to about 22 carbon atoms. Examples of suitable benzoate esters include, but are not limited to, the commercial products FINSOLV TN, benzoic acid esterified with fatty alcohols including about 12 to about 15 carbon atoms; FINSOLV SB, isostearyl benzoate; FINSOLV P, PPG-15 stearyl ether benzoate; or combinations thereof, all available from Finetex Inc., Elmwood Park, N.J.

Examples of other specific water-insoluble conditioning compounds that can be incorporated into the conditioning shampoos of the present invention include, but are not limited to, polysiloxane polyether copolymers; acetylated lanolin alcohols; lanolin-derived extract of sterols and sterol esters; lanolin alcohol concentrate; isopropyl ester of lanolin fatty acids; polyol fatty acid; keratin protein derivatives; amino-functional silicones; fatty alcohol fraction of lanolin; mineral oil and lanolin alcohol mixture; high molecular weight esters of lanolin; vinylpyrrolidone/dimethylaminoethylmethacrylate copolymer; 5 mole ethylene oxide adduct of soya sterol; 10 mole ethylene oxide adduct of soya sterol; stearic acid ester of ethoxylated methyl glucoside; hydroxylated lanolin; lactamide MEA; stearamide MEA; mixed ethoxylated and propoxylated long chain alcohols; hydrolyzed animal keratin; ethyl hydrolyzed animal keratin; avocado oil; sweet almond oil; grape seed oil; jojoba oil; apricot kernel oil; sesame oil; hybrid safflower oil; wheat germ oil; ethyl esters of hydrolyzed animal protein; blend of cetyl and stearyl alcohols with ethoxylated cetyl or stearyl alcohols; propoxylated (1–10 moles) lanolin alcohols; isostearamide DEA; and hydrolyzed collagen protein. Other water-insoluble conditioning agents are listed in *CTFA Cosmetic Ingredient Handbook, First Edition,* The Cosmetic Toiletry and Fragrance Association, Inc., New York, N.Y. (1988), pp. 71–73, hereby incorporated by reference.

In accordance with another important embodiment of the present invention, the shampoo composition of the present invention is an antidandruff shampoo wherein the water-insoluble hair treating compound is an antidandruff agent. The antidandruff agent usually is a particulate compound that is capable of relieving the symptoms of dandruff and is substantive to the hair and scalp to impart residual antidandruff properties between shampoos. Examples of particulate compounds exhibiting antidandruff properties include, but are not limited to, salicylic acid, elemental sulfur, selenium sulfide, zinc pyrithione, a water-insoluble 1-hydroxy pyridone, an azole antimycotic, and undecylenic acid. Particularly advantageous antidandruff agents useful in the shampoo composition of the present invention are zinc pyrithione and elemental sulfur. Zinc pyrithione is the zinc complex of 2-pyridinethiol-1-oxide, and is available commercially from Olin Corp. under the brand name of ZINC OMADINE. Useful sulfurs include elemental sulfur of sufficient purity and particle size to function as an antidandruff agent, as is well known to those skilled in the art.

The antidandruff agents are extremely water insoluble and, therefore, are present in the antidandruff shampoo composition as discrete solid particles. These particles should be homogeneously dispersed and suspended throughout the shampoo to ensure the consumer receives an efficacious dose of the antidandruff agent at each shampooing. Without a suspending agent, the antidandruff agent can completely separate from the antidandruff shampoo composition resulting in poor dandruff control, and ultimately in consumer dissatisfaction and complaints. Therefore, a suspending agent composition must be incorporated into the basic antidandruff formulation to retard, minimize or eliminate settling of the insoluble antidandruff agent. In general, the suspending agent of the present invention effectively suspends a particulate antidandruff agent, and other particulate and liquid hair treating compounds.

In addition to the cleansing surfactant and the water-insoluble hair treating compound, a hair shampoo of the present invention also includes a suspending agent. The suspending agent maintains the water-insoluble hair treating compound homogeneously dispersed throughout the composition for at least the expected life of the product, and does not adversely affect the foaming, cleansing, conditioning, antidandruff or other hair treating properties of the shampoo.

Many suspending agents operate on the principle of thickening the composition to a sufficient viscosity to retard the settling or separation of the water-insoluble hair treating compound to such an extent that the composition is stable over its expected lifetime. However, considering the relatively high percentage of water-insoluble hair treating compound included in shampoos, a suspending agent that relies only on thickening often is incorporated into the composition in such a high percentage that an unacceptably viscous product results. Shampoo compositions having such a high viscosity are not acceptable to consumers because the compositions are difficult to dispense, difficult to spread evenly on the hair and scalp, and often do not generate an adequate foam.

Accordingly, a shampoo composition of the present invention includes a suspending agent, comprising an amine having the general structural formula (I) or (II) or (III) and a suitable acid, that does not rely merely on thickening to suspend the water-insoluble hair treating compound. The amine is present in an amount of about 1% to about 10%, and preferably about 1.5% to about 5%, by weight of the composition; the acid is present in a sufficient amount such that essentially no solid particles of the amine of structural formula (I) or (II) or (III) are present in the composition. Therefore, in general, the acid is present in an amount of about 0.05% to about 5% by weight of the composition.

In accordance with an important feature of the present invention, an amine useful in the present invention is depicted by the general structural formula

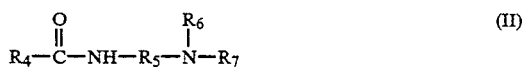

(I) or (II) or (III), wherein $R_1$ is an alkyl group, straight chain or branched, including at least 16 carbon atoms; $R_2$ and $R_3$ are, independently, selected from the group consisting of hydrogen, an alkyl group including one to about 22 carbon atoms, benzyl and phenyl; $R_4$ is an alkyl group, straight chain or branched, including at least 13 carbon atoms; $R_5$ is an alkylene moiety including 1 to 4 carbon atoms; $R_6$ and $R_7$ are, independently, an alkyl group including 1 to 4 carbon atoms; and $R_8$ and $R_9$ are, independently, hydrogen or an alkyl group including 1 to 4 carbon atoms.

The alkyl groups $R_1$ and $R_4$ of the amine of general structural formulas (I), (II), and (III) can be derived from a fatty acid, and therefore do not have to be solely, or primarily, of one chain length, i.e., the long chain need not be derived only from cetyl ($C_{16}$) or stearyl ($C_{18}$). Rather, a compound of general structural formula (I) or (II) or (III) wherein the alkyl group $R_1$ or $R_4$ is a mixture of lengths can be used, as long as the amine is water insoluble and includes at least one alkyl group of sufficient chain length to impart water insolubility. Such amine compounds are prepared conveniently from naturally occurring materials, such as tallow, soya oil and the like, or from synthetically produced mixtures.

In particular, an amine of general structural formula (I) is a primary, a secondary or a tertiary amine including at least one alkyl group including at least 16 carbon atoms and is a solid compound at room temperature. It should be understood that a commercial amine of general structural formula (I), and having at least one carbon chain of at least 16 carbon atoms as the predominant chain length also can include a minor amount of an amine having a carbon chain of fewer than 16 carbon atoms. A minor amount of an amine having carbon chain including less than 16 carbon atoms, e.g., up to about 5% by weight of the amine present in the composition, does not adversely affect the composition. Suitable amines of general structural formula (I) are solid compounds at room temperature, and are water-insoluble compounds exhibiting a water solubility of 0.5 g (grams) or less per 100 ml (milliliters) of water.

When an amine of general structural formula (I) is sufficiently neutralized such that essentially no solid particles of the amine are present in the composition, the neutralized amine forms a network that suspends the water-insoluble hair treating compound, such as a silicone conditioning agent or an antidandruff agent. The network effectively suspends the water-insoluble hair treating compound at least for the expected life of the product, e.g., about one year, without adversely affecting the other properties of the shampoo composition, like foam generation.

Specific primary amines of general structural formula (I) useful in a shampoo composition of the present invention include, but are not limited to, $C_{20-22}$ amine, soya amine, hydrogenated tallow amine, stearyl amine, tallow amine, oleyl amine, hexadecylamine, octadecylamine, and combinations thereof. Suitable secondary amines include, but are not limited to, di(hydrogenated tallow)amine, disoyamine, dipalmityl amine, and combinations thereof. Suitable tertiary amines includes, but are not limited to, tri(hydrogenated tallow)amine, di(-hydrogenated tallow) methylamine, distearyl methyl amine, methyl dibehenamine, dimethyl behenamine, dimethyl tallowamine, dimethyl stearamine, dimethyl tetradecylamine, dimethyl hexadecyl amine, dimethyl octadecyl amine, dimethyl soyamine, dimethyl oleyl amine, stearyl methyl benzyl amine, dimethyl palmitamine, dimethyl (hydrogenated tallow)amine, and combinations thereof. The shampoo compositions also can include a combination of primary and/or secondary and/or tertiary amines having the general structural formula (I).

As stated above, a suitable amine also can have a distribution of alkyl groups wherein the predominant alkyl group includes at least 16 carbon atoms and wherein a minor portion, such as 5% or less, of the alkyl groups include less than 16 carbon atoms. It also should be understood that a diamine of general structural formula (III) is a suitable amine. Exemplary diamines include, but are not limited to, hydrogenated tallow diamine, tallow diamine, soya diamine or oleyl diamine, having the structural formula (V):

$$R_1NH(CH_2)_nNH_2, \qquad (V)$$

wherein n is a number 1 through 4 and $R_1$ is an alkyl group including at least 16 carbon atoms.

In addition to an amine of general structural formula (I) or (III), an amine of general structural formula (II) also can be included in the shampoo composition as the amine, either alone or in combination with an amine of general structural formula (I) or (III). A useful amine of general structural formula (II), generally termed an amidoamine, is a water-insoluble compound having a water solubility of 0.5 g or less per 100 ml of water. Examples of an amine of general structural formula (II) include, but are not limited to, stearamidopropyl diethylamine, stearamidoethyl diethylamine, stearamidoethyl dimethylamine, palmitamidopropyl dimethylamine, behenamidopropyl dimethylamine, myristamidopropyl dimethylamine, oleamidopropyl dimethylamine, ricinoleamidopropyl dimethylamine, stearamidopropyl dimethylamine, and combinations thereof.

In addition to an amine having the general structural formula (I) or (II) or (III), the suspending agent of the shampoo composition also includes a suitable acid. To provide a suspending agent that effectively suspends the water-insoluble hair treating compound in the shampoo composition, a sufficient amount of an inorganic mineral acid or an organic carboxylic acid, either aliphatic or aromatic, is included in the composition to neutralize the amine such that essentially no solid particles of the amine are present in the composition. Accordingly, the acid used to neutralize the amine compound is of sufficient acid strength to neutralize a free amine nitrogen. Such acids include, but are not limited to, the inorganic mineral acids, like hydrochloric acid, sulfuric acid, nitric acid, phosphoric acid, and combinations thereof.

It also has been found that an aliphatic carboxylic acid including up to about 22 carbon atoms, or an aromatic carboxylic acid, can be used to neutralize the amine of general structural formula (I) or (II) or (III). Preferably, the aliphatic carboxylic acid is a saturated aliphatic acid and includes up to about 16 carbon atoms. An aliphatic carboxylic acid including more than about 16 carbon atoms, or including an olefinic unsaturation, is useful in the present composition, but provides a composition having somewhat decreased esthetic properties compared to compositions including a saturated acid having about 16 or fewer carbon atoms. Therefore, examples of suitable aliphatic carboxylic acids include, but are not limited to, acetic acid, lactic acid, citric acid, tartaric acid, propionic acid, butyric acid, pentanoic acid, glycolic acid, decanoic acid, lauric acid, palmitic acid, octanoic acid and combinations thereof. Oleic acid and stearic acid are nonlimiting examples of acids including more than 16 carbon atoms and/or an olefinic unsaturation that are useful in the present invention.

Examples of suitable aromatic carboxylic acids include, but are not limited to, benzoic acid, phthalic acid, salicylic acid, isophthalic acid, terephthalic acid, toluic acid, and combinations thereof. Alkyl-substituted aromatic acids also are useful in a composition of the present invention. An aliphatic carboxylic acid, aromatic carboxylic acid or mineral acid can be the sole acid included in the shampoo composition, or any combination of the three types of acid can be included in the composition. In general, a sufficient amount of acid is added to the composition such that essentially no solid particles of the amine are present in the composition and to adjust the final pH of the shampoo composition of about 3 to about 8, and more preferably to a pH of about 5 to about 7. An excess amount of acid does not adversely affect the composition.

In addition to the above-described essential ingredients, other common cosmetic components and additives can be included in the shampoo composition of the present invention to impart desirable or esthetic properties, as long as the basic properties of the shampoo composition are not adversely affected. Such optional cosmetic components and additives include, but are not limited to, nonionic surfactants, amphoteric surfactants, fragrances, dyes, hair colorants, opacifiers, pearlescing agents, thickeners, inorganic salts, humectants, hydrotropes, foam stabilizers, solubilizers, preservatives, water softening agents, buffers and the like. These optional components and additives usually are present in weight percentages of 0% up to about 5% by weight of the shampoo composition each, and usually 0% to about 20% by weight of the shampoo composition in total.

The composition also can include optional conditioning agents and emulsifiers. In general, such optional conditioning agents and emulsifiers, like quaternary ammonium compounds, are well-known to those skilled in the art, and can be included in the present shampoo composition in an amount of 0% to about 5% by weight of the composition.

The carrier of the shampoo composition is predominantly water, but nonaqueous solvents also can be included to help solubilize composition ingredients that are not sufficiently soluble in water, to adjust the viscosity of the composition or to act as a humectant. Suitable solvents include polyols, like glycerol; glycols, like ethylene glycol, propylene glycol and hexylene glycol; or mixtures thereof. The optional nonaqueous solvents should not adversely affect the ability of the composition to cleanse and treat the hair and scalp, or adversely affect consumer appeal of the composition. A nonaqueous solvent can be present in the hair shampoo-conditioner composition of the present invention in an amount ranging from 0% up to about 5% by weight of the composition.

To achieve the full advantage of the present invention, the shampoo composition is a moderately viscous mixture, having a viscosity in the range of from about 1000 cps (centipoises) to about 15,000 cps, that is stable indefinitely at temperatures normally found in commercial product storage and shipping. A shampoo composition of the present invention generally is a suspension that is stable and that resists phase separation or settling of composition ingredients at a temperature of about 20° C. to about 25° C. essentially indefinitely. The compositions also have demonstrated sufficient stability to phase separation and settling of ingredients at temperatures normally found in commercial product storage and shipping to remain unaffected for periods of one year or more.

In accordance with the method of the present invention, several shampoo compositions were prepared, then applied to human hair, to demonstrate the improved suspending properties and the ability of the shampoo composition to deliver a water-insoluble hair treating compound to the hair or scalp provided by a composition comprising a cleansing surfactant; a water-insoluble hair treating compound; and a suspending agent comprising an amine compound of general structural formula (I) or (II) or (III) and a suitable acid. It has been demonstrated that to maximize suspension properties, the shampoo composition of the present invention should include the amine and the acid in a sufficient amount such that essentially no solid particles of the amine are present in the composition.

It should be noted, however, that the acid is not necessarily present in an equimolar, or equimolar equivalent, amount in relation to the amine. A stoichiometric amount of acid in relation to the amine is not necessarily required because other ingredients in the shampoo composition may neutralize the amine. Therefore, a stoichiometric amount of acid can be included in the composition. However, as little as 20% of the stoichiometric amount of acid can be added to sufficiently neutralize the amine depending upon the particular composition ingredients and the desired pH for the composition. An excess amount of acid does not adversely effect the stability of the composition, but also does not increase stability, and therefore is wasted except for the purposes of adjusting a composition property, such as pH.

Although the mechanism of interaction between the amine, the acid and other composition ingredients is not known precisely, it has been theorized that the acid-neutralized amine forms a network that suspends the water-insoluble hair treating compound. It should be noted that a shampoo composition including only free amine, i.e., an amine compound of general structural formula (I) or (II) or (III) not neutralized with an acid, underwent a phase separation relatively rapidly, such as in less than 24 hours. Accordingly, it is the acid-neutralized amine compound that suspends the water-insoluble hair treating compound in the shampoo composition. Furthermore, laboratory and salon tests have shown that hair shampooed with a composition of the present invention is effectively cleansed and that the water-insoluble hair treating compound is effectively delivered to the hair or scalp.

To demonstrate the new and unexpected results achieved by the method and composition of the present invention, the following Examples 1 through 20 were prepared by an identical method, wherein the anionic cleansing surfactant, as an approximately 30% by weight aqueous solution, first was added to a vessel, then heated to about 180° F. under moderate agitation. Then the amine compound was added to the vessel, followed by the acid. The resulting mixture was maintained at about 180° F., and stirred for about 30 to about 90 minutes to homogenize the mixture. The remaining amount of water was added to cool the mixture, then the remaining ingredients were added to the resulting mixture individually, in any desired order. Agitation speed was increased after addition of the water-insoluble hair treating compound to effectively disperse the water-insoluble hair treating compound throughout the composition.

| Ingredient | EX. 1[1] | EX. 2 | EX. 3 | EX. 4 | EX. 5 |
|---|---|---|---|---|---|
| Ammonium Lauryl Sulfate[2] | 6.0 | 6.0 | 6.0 | 6.0 | 6.0 |
| Sodium Lauryl Sulfate[3] | 4.5 | 4.5 | 4.5 | 4.5 | 4.5 |
| Ammonium Lauryl Ether Sulfate | 2.8 | 2.8 | 2.8 | 2.8 | 2.8 |
| Lauramide DEA | 1.25 | 1.25 | 1.25 | 1.25 | 1.25 |
| ADOGEN 232[4] | 3.0 | 3.0 | 3.0 | 3.0 | 3.0 |

| Ingredient | EX. 1 | EX. 2 | EX. 3 | EX. 4 | EX. 5 |
|---|---|---|---|---|---|
| ADOGEN 140[5] | — | — | — | — | — |
| ADOGEN 240[6] | — | — | — | — | — |
| ADOGEN 540D[7] | — | — | — | — | — |
| Citric Acid[8] | 0.55 | 0.55 | 0.55 | 0.55 | — |
| Lactic Acid[9] | — | — | — | — | 0.79 |
| Sulfuric Acid[10] | — | — | — | — | — |
| Phosphoric Acid[11] | — | — | — | — | — |
| Hydrochloric Acid[12] | — | — | — | — | — |
| Silicone Blend[13] | 2.00 | 2.00 | 2.00 | 2.00 | 2.00 |
| Tetrasodium EDTA[14] | 0.08 | 0.08 | 0.08 | 0.08 | 0.08 |
| Dye | 0.11 | 0.11 | 0.11 | 0.11 | 0.11 |
| Fragrance | 0.50 | 0.50 | 0.50 | 0.50 | 0.50 |
| Preservative[15] | 0.13 | 0.13 | 0.13 | 0.13 | 0.13 |
| Ammonium Xylene Sulfonate | 0.18 | 0.18 | 0.18 | 0.18 | 0.18 |
| Soft Water | q.s. | q.s. | q.s. | q.s. | q.s. |
| Appearance: | pearlescent | pearlescent | pearlescent | pearlescent | pearlescent |
| pH: | 5.3 | 5.4 | 5.3 | 5.7 | 5.5 |
| Viscosity (in cps)[16]: | 3230 | 3010 | 2650 | 3700 | 1780 |

| Ingredient | EX. 6 | EX. 7 | EX. 8 | EX. 9 | EX. 10 |
|---|---|---|---|---|---|
| Ammonium Lauryl Sulfate[2] | 6.0 | 6.0 | 6.0 | 6.0 | 6.0 |
| Sodium Lauryl Sulfate[3] | 4.5 | 4.5 | 4.5 | 4.5 | 4.5 |
| Ammonium Lauryl Ether Sulfate | 2.8 | 2.8 | 2.8 | 2.8 | 2.8 |
| Lauramide DEA | 1.25 | 1.25 | 1.25 | 1.25 | 1.25 |
| ADOGEN 232[4] | — | — | — | 3.0 | 3.0 |
| ADOGEN 140[5] | 3.0 | 3.0 | 3.0 | — | — |
| ADOGEN 240[6] | — | — | — | — | — |
| ADOGEN 540D[7] | — | — | — | — | — |
| Citric Acid[8] | — | — | — | — | — |
| Lactic Acid[9] | 0.84 | 0.88 | 0.66 | 0.71 | 0.70 |
| Sulfuric Acid[10] | — | — | — | — | — |
| Phosphoric Acid[11] | — | — | — | — | — |
| Hydrochloric Acid[12] | — | — | — | — | — |
| Silicone Blend[13] | 2.0 | 2.0 | 2.0 | 2.0 | 2.0 |
| Tetrasodium EDTA[14] | 0.08 | 0.08 | 0.08 | 0.08 | 0.08 |
| Dye | 0.11 | 0.11 | 0.11 | 0.11 | 0.11 |
| Fragrance | 0.50 | 0.50 | 0.50 | 0.50 | 0.50 |
| Preservative[15] | 0.13 | 0.13 | 0.13 | 0.13 | 0.13 |
| Ammonium Xylene Sulfonate | 0.18 | 0.18 | 0.18 | 0.18 | 0.18 |
| Soft Water | q.s. | q.s. | q.s. | q.s. | q.s. |
| Appearance: | pearlescent | pearlescent | pearlescent | pearlescent | pearlescent |
| pH: | 7.4 | 5.8[17] | 6.0[18] | 6.0 | 6.1 |
| Viscosity (in cps)[16]: | 4320 | 1880 | 4220 | 2300 | 2250 |

| Ingredient | EX. 11 | EX. 12 | EX. 13 | EX. 14 | EX. 15 |
|---|---|---|---|---|---|
| Ammonium Lauryl Sulfate[2] | 6.0 | 6.0 | 6.0 | 6.0 | 6.0 |
| Sodium Lauryl Sulfate[3] | 4.5 | 4.5 | 4.5 | 4.5 | 4.5 |
| Ammonium Lauryl Ether Sulfate | 2.8 | 2.8 | 2.8 | 2.8 | 2.8 |
| Lauramide DEA | 1.25 | 1.25 | 1.25 | 1.25 | 1.25 |
| ADOGEN 232[4] | — | — | — | — | — |
| ADOGEN 140[5] | — | — | — | — | — |
| ADOGEN 240[6] | 3.0 | 3.0 | 3.0 | 3.0 | 3.0 |
| ADOGEN 540D[7] | — | — | — | — | — |
| Citric Acid[8] | — | — | 0.55 | — | — |
| Lactic Acid[9] | 0.70 | 0.62 | — | — | — |
| Sulfuric Acid[10] | — | — | 0.15 | — | — |
| Phosphoric Acid[11] | — | — | — | 0.26 | 0.51 |
| Hydrochloric Acid[12] | — | — | — | — | — |
| Silicone Blend[13] | 2.00 | 2.00 | 2.00 | 2.00 | 2.00 |
| Tetrasodium EDTA[14] | 0.08 | 0.08 | 0.08 | 0.08 | 0.08 |
| Dye | 0.11 | 0.11 | 0.11 | 0.11 | 0.11 |
| Fragrance | 0.50 | 0.50 | 0.50 | 0.50 | 0.50 |
| Preservative[15] | 0.13 | 0.13 | 0.13 | 0.13 | 0.13 |
| Ammonium Xylene Sulfonate | 0.18 | 0.18 | 0.18 | 0.18 | 0.18 |
| Soft Water | q.s. | q.s. | q.s. | q.s. | q.s. |
| Appearance: | pearlescent | pearlescent | pearlescent | pearlescent | pearlescent |
| pH: | 5.6 | 5.9 | 8.1 | 7.0 | 5.7 |
| Viscosity (in cps)[16]: | 11,500 | 7100 | 10,600 | 7580 | 9980 |

| Ingredient | EX. 16 | EX. 17 | EX. 18 | EX. 19 | EX. 20 |
|---|---|---|---|---|---|
| Ammonium Lauryl Sulfate[2] | 6.0 | 6.0 | 6.0 | 6.0 | 9.3 |
| Sodium Lauryl Sulfate[3] | 4.5 | 4.5 | 4.5 | 4.5 | 5.0 |
| Ammonium Lauryl Ether Sulfate | 2.8 | 2.8 | 2.8 | 2.8 | 1.6 |
| Lauramide DEA | 1.25 | 1.25 | 1.25 | 1.25 | 0.7 |
| ADOGEN 232[4] | — | — | — | — | — |
| ADOGEN 140[5] | — | — | — | — | — |
| ADOGEN 240[6] | 3.0 | 3.0 | 3.0 | 3.0 | — |
| ADOGEN 540D[7] | — | — | — | — | 5.0 |
| Citric Acid[8] | — | — | — | — | 2.0 |
| Lactic Acid[9] | — | — | — | — | — |
| Sulfuric Acid[10] | 0.30 | — | — | — | — |
| Phosphoric Acid[11] | — | — | — | — | — |
| Hydrochloric Acid[12] | — | 0.22 | 0.20 | 0.20 | — |
| Silicone Blend[13] | 2.00 | 2.00 | 2.00 | 2.00 | 2.00 |
| Tetrasodium EDTA[14] | 0.08 | 0.08 | 0.08 | 0.08 | 0.08 |
| Dye | 0.11 | 0.11 | 0.11 | 0.11 | q.s. |
| Fragrance | 0.50 | 0.50 | 0.50 | 0.50 | — |
| Preservative[15] | 0.13 | 0.13 | 0.13 | 0.13 | 0.15 |
| Ammonium Xylene Sulfonate | 0.18 | 0.18 | 0.18 | 0.18 | 0.10 |
| Soft Water | q.s. | q.s. | q.s. | q.s. | q.s. |
| Appearance: | pearlescent | pearlescent | pearlescent | pearlescent | pearlescent |
| pH: | 6.2 | 5.5 | 6.3 | 6.3 | 5.9 |
| Viscosity (in cps)[16]: | 8820 | 10,260 | 4500 | 4100 | — |

[1] Percent by weight of active ingredient in the composition;
[2] Added as a 30% by weight active solution;
[3] Added as a 30% by weight active solution;
[4] A secondary amine based on 85-90% by weight straight chain alcohols and 10-15% by weight branched alcohols including about 16 to about 22 carbon atoms, available from Sherex Chemical Co., Inc. Dublin, Ohio;
[5] Hydrogenated tallow amine, a primary amine available from Sherex Chemical Co., Dublin, Ohio;
[6] Di(hydrogenated tallow)amine, a secondary amine available from Sherex Chemical Co., Dublin, Ohio;
[7] Hydrogenated tallow diamine, a diamine available from Sherex Chemical Co., Dublin, Ohio;
[8] Added as a 50% by weight aqueous solution;
[9] Added as an 88% by weight aqueous solution;
[10] Added as a 50% by weight aqueous solution;
[11] Added as an 85-88% by weight aqueous solution;
[12] Added as a 36% by weight aqueous solution;
[13] Added as a 100% active blend including one part by weight Silicone GUM SE-30, a polydimethylsiloxane having a viscosity of about 15 × 10$^6$ to about 30 × 10$^6$ centipoises, and two parts by weight of Silicone Fluid 96-350, a polydimethylsiloxane having a viscosity of about 350 centipoises, both available from General Electric Silicone Products Division, Waterford, NY;
[14] Added as a 39% aqueous solution of tetrasodium ethylenediaminetetraacetate;
[15] DMDM hydantoin, methylisothiazolinone and methylchloroisothiazolinone;
[16] Viscosity in centipoises;
[17] pH after preparation of the composition was 4.37, then the pH was adjusted to 5.8 with sodium hydroxide; and
[18] pH after preparation of the composition was 7.7, then the pH was adjusted to 6.0 with lactic acid.

The compositions of Examples 1–4 were identical except the composition of Examples 1 and 4 were emulsified at about 180° F. for 30 minutes, whereas the composition of Example 2 was emulsified for 60 minutes and the composition of Example 3 was emulsified for 90 minutes. The shampoo-conditioner compositions of Examples 1–4 were essentially identical, with each composition maintaining phase stability at 110° F. and 120° F. after 24 hours. The dispersed silicone droplets resisted phase separation and were effectively deposited on the hair to impart hair conditioning properties to the treated hair. The composition of Example 5 was similar to the compositions of Examples 1 through 4 except lactic acid was substituted for citric acid. The composition of Example 5 demonstrated properties essentially identical to the compositions of Examples 1–4. Accordingly, stable shampoo-conditioner compositions resulted from emulsifying the ingredients for at least 30 minutes, and substitution of an organic aliphatic carboxylic acid for an inorganic mineral acid did not adversely effect composition stability. The compositions of Examples 9 and 10 were essentially identical repeats of the composition of Example 5, except the compositions of Examples 9 and 10 were phase stable one week after preparation.

The compositions of Examples 6 through 8 utilized a primary amine and lactic acid. The compositions exhibited essentially no silicone separation after storage at 110° F. or at 120° F. for 6 months.

The compositions of Examples 11 through 19 utilized a different secondary amine (ADOGEN 240) and varied the acid used in the suspending agent. The compositions of Examples 11-19 each effectively resisted phase separation at 110° F. and 120° F. for a period of at least six months and demonstrated that the acid of the suspending agent can be an organic carboxylic acid or an inorganic mineral acid. The composition of Example 20 utilized a diamine of general structural formula (III) (ADOGEN 540D). The composition of Example 20 effectively resisted phase separation after two months storage at room temperature, at 110°, and at 120° F.

To further demonstrate the ability of an amine having the general structural formula (I) or (II) or (III) and a suitable acid to suspend a water-insoluble hair treating compound, different combinations of various amines and various acids were tested for an ability to suspend a silicone blend, or a combination of a silicone blend and sulfur, in water. In each test, the aqueous solution included 2% by weight of a silicone blend including one part by weight Silicone GUM SE-30 and 2 parts by weight SF 96-350 Silicone Fluid. The solution did not include a cleansing surfactant. Therefore, from the compositions listed in TABLE I, wherein each composition was absent a cleansing surfactant, it was shown that the combination of the amine and the acid suspends the silicone and, when present, the sulfur. In the compositions of Examples 21 through 40, summarized in TABLE I, the amine was present in an amount of from about 3% to about 5% by weight; the acid was present in an amount of from about 0.5% to about 1.6% by weight.

TABLE I

Suspending Agents Including an Amine and an Acid

| Example | Amine | Acid |
|---|---|---|
| 21 | Hydrogenated Tallow Amine[1] (3%)[2] | Phthalic Acid (0.95%)[3] |
| 22 | Hydrogenated Tallow Amine (3%) | Salicylic Acid (1.58%) |
| 23[4] | ADOGEN 232[5] (3%) | Phthalic Acid (0.50%) |
| 24 | ADOGEN 232 (3%) | Citric Acid (0.50%) |
| 25 | ADOGEN 232 (3%) | Phosphoric Acid (0.80%) |
| 26 | Di(Hydrogenated Tallow) Amine[6] (3%) | Phthalic Acid (0.50%) |
| 27 | Di(Hydrogenated Tallow) Amine (3%) | Salicylic Acid (0.86%) |
| 28 | Di(Hydrogenated Tallow) Amine (3%) | Citric Acid (0.45%) |
| 29 | Di(Hydrogenated Tallow) Amine (3%) | Benzoic Acid (1.00%) |
| 30 | Distearyl Amine[7] (3%) | Phthalic Acid (0.50%) |
| 31 | Distearyl Amine (3%) | Salicylic Acid (0.84%) |
| 32 | Distearyl Amine (3%) | Benzoic Acid (1.00%) |
| 33 | Tri(Hydrogenated Tallow) Amine[8] (3%) | Phthalic Acid (0.34%) |
| 34 | Tri(Hydrogenated Tallow) Amine (3%) | Salicyclic Acid (0.58%) |
| 35 | Di(Hydrogenated Tallow) Methyl Amine[9] (3%) | Phthalic Acid (0.49%) |
| 36 | Di(Hydrogenated Tallow) Methyl Amine (3%) | Salicylic Acid |

TABLE I-continued

Suspending Agents Including an Amine and an Acid

| Example | Amine | Acid |
|---|---|---|
|  | Amine (3%) | (0.84%) |
| 37 | Distearyl Methyl Amine[10] (3%) | Phthalic Acid (0.48%) |
| 38 | Distearyl Methyl Amine (3%) | Salicylic Acid (0.82%) |
| 39 | Stearamidopropyl Dimethylamine[11] (3%) | Citric Acid (0.53%) |
| 40 | Stearamidoethyl Diethylamine[12] (5%) | Citric Acid (0.55%) |

[1]ADOGEN 140, a primary amine, available, as are all other ADOGEN amines, from Sherex Chemical Co., Dublin, Ohio;
[2]percent by weight of amine in the composition;
[3]percent by weight of acid in the composition;
[4]composition includes 2% silicone blend and 6.37% sulfur-Carbopol slurry (2.03% elemental sulfur);
[5]secondary amine including 85-90% by weight straight chain alcohols and 10-15% by weight branched alcohols including from about 16 to about 22 carbon atoms;
[6]ADOGEN 240, a secondary amine;
[7]ADOGEN 249, a secondary amine;
[8]ADOGEN 340, a tertiary amine;
[9]ADOGEN 343, a tertiary amine;
[10]ADOGEN 349, a tertiary amine;
[11]LEXAMINE S-13, an amine of general structural formula (II), available from Inolex Chemical Div., Philadelphia, PA.; and
[12]LEXAMINE 22, an amine of general structural formula (II), available from Inolex Chemical Div., Philadelphia, PA.

Each composition of Examples 21 through 40 was a stable composition that effectively suspended the silicone and the sulfur after storage at room temperature and at 120° F. for 3 months. In some of the compositions, such as 21, 22, 30, 31, 32, and 39, a slight phase separation was observed. However, the separated phase did not include silicone. Therefore, the silicone was effectively suspended by the suspending agent of the present invention. In compositions including a tertiary amine, it was found that flocculation, or curdling, of the composition can occur after one day of storage at 120° F. (composition of Examples 33 and 34), however the silicone remains suspended in the composition.

Overall, the compositions of Examples 21 through 40 of TABLE I show that a primary, secondary, or tertiary amine having the general structural formula (I) or (III), or an amine having the general structural formula (II), when neutralized with a sufficient amount of a suitable acid, effectively suspends a water-insoluble hair treating compound, either liquid or particulate, in an aqueous composition. Further, TABLE I, and Examples 1-20, show that an inorganic mineral acid (e.g., composition of Example 25), an aliphatic carboxylic acid (e.g., composition of Examples 24 and 28) or an aromatic carboxylic acid (e.g., composition of Examples 21-23, 26-27, and 29-40) is a suitable acid to neutralize the amine. TABLE I also shows that an amine of general structural formula (I) (Examples 21-38) or that an amine of general structural formula (II) (Examples 39 and 40), after neutralization by a sufficient amount of a suitable acid, effectively suspend a water-insoluble hair treating compound in a hair shampoo composition.

To further demonstrate the stability of a shampoo composition of the present invention, various amines and acids, in varying amounts, were used as the suspending agent in a composition that included 2% by weight of a water-insoluble silicone blend of 1 part Silicone GUM SE-30 and 2 parts by weight SF 96-350 Silicone Fluid; 12.10% by weight, in total, of the anionic surfactants ammonium lauryl sulfate, ammonium lauryl ether sulfate (1 mole EO) and sodium lauryl sulfate; and 0.90% of the alkanolamide lauramide DEA. TABLE II lists the particular amine and particular acid used in each compositions of Examples 41 through 60, the amount of amine and acid included in each composition, and the stability of each composition. The percentages included in TABLE II are the weight percentages of the active amount of amine and acid included in each composition.

TABLE II

Stability of Shampoo Compositions Including an Amine-Acid Suspending Agent

| Example | Amine | Acid | Stability |
|---|---|---|---|
| 41 | ADOGEN 140 (3%) | LACTIC 0.84% | Stable at room temperature, unstable at 120° F., silicone suspended at both temp. |
| 42 | ADOGEN 140 (3%) | LACTIC 0.88% | Stable at room temperature, unstable at 120° F., silicone suspended at both temp. |
| 43 | ADOGEN 140 (2.5%) | LACTIC 0.70% | Stable at room temperature, unstable at 120° F., silicone suspended at both temp. |
| 44 | ADOGEN 140 (2.0%) | LACTIC 0.56% | Stable at room temperature, unstable at 120° F., silicone suspended at both temp. |
| 45 | ADOGEN 232 (3%) | CITRIC 0.55% | Stable at all temp., mucilaginous at 120° F. |
| 46 | ADOGEN 232 (2.5%) | CITRIC 0.45% | Stable at all temp., mucilaginous at 120° F. |
| 47 | ADOGEN 232 (2.0%) | CITRIC 0.35% | Stable at all temp., mucilaginous at 120° F. |
| 48 | ADOGEN 232 (1.5%) | CITRIC 0.25% | Stable at all temp., mucilaginous at 120° F. |
| 49 | ADOGEN 232 (3%) | LACTIC 0.79% | Stable at all temp., mucilaginous at 120° F. |
| 50 | ADOGEN 232 (2.5%) | LACTIC 0.66% | Stable at all temp., mucilaginous at 120° F. |
| 51 | ADOGEN 232 (2.0%) | LACTIC 0.53% | Stable at all temp., mucilaginous at 120° F. |
| 52 | ADOGEN 232 (1.5%) | LACTIC 0.40% | Stable at all temp., mucilaginous at 120° F. |
| 53 | ADOGEN 232 (3%) | CITRIC 1.58% | Stable at all temp., mucilaginous at 120° F. |
| 54 | ADOGEN 240 (3%) | LACTIC 0.62% | Stable at all temp. |
| 55 | ADOGEN 240 (3%) | PHOSPHORIC 0.51% | Stable at all temp. |
| 56 | ADOGEN 240 (3%) | SULFURIC 0.30% | Stable at all temp. |
| 57 | ADOGEN 240 (3%) | HYDRO-CHLOR-IC 0.22% | Stable at all temp. |
| 58 | ADOGEN 240 (2.5%) | HYDRO-CHLOR-IC 0.18% | Stable at all temp. |
| 59 | ADOGEN 240 (2.0%) | HYDRO-CHLOR-IC 0.14% | Stable at all temp. |
| 60 | ADOGEN 240 (3.0%) | HYDRO-CHLOR-IC 0.22% | Stable at all temp. |

TABLE II shows that a variety of amines having general structural formula (I) can be neutralized with a variety of inorganic acids or organic carboxylic acids to provide an effective suspending agent for a shampoo composition including a water-insoluble hair treating compound. In addition, compositions of Examples 54 through 60 were subjected to laboratory and beauty center evaluations, and found to have physical and esthetic properties, such as pearl, wet and dry combing, cleansing performance, lather and feel, that equal the properties exhibited by SUAVE, a leading hair shampoo conditioner composition available commercially from Helene Curtis, Inc., Chicago, Ill.

To demonstrate the effect of varying the amount of acid in the composition, the secondary amine di(hydrogenated tallow)amine (ADOGEN 240), at 3% by weight, was included in a composition further including 12.10% by weight in total of anionic cleansing surfactants. Varying amounts of citric acid were included to determine the effects of an increased amount of acid in the composition on the ability of the ADOGEN 240 and citric acid to suspend a water-insoluble hair treating compound and to provide an esthetically pleasing, and therefore consumer acceptable, shampoo composition. TABLE III summarizes the compositions of Examples 61 through 71, showing the amount of citric acid included in the composition (Examples 61–66), and the different the water-insoluble hair treating compounds included in the composition (Examples 63, 67, and 68). TABLE III also illustrates compositions including a fatty acid having more than 12 carbon atoms as the acid of the suspending agent (Examples 69–72).

TABLE III

Effect of an Increased Amount of Acid in the Suspending Agent and Effect of Using a Fatty Acid in the Suspending Agent

| EX. | Amount of Acid | pH | Water-Insoluble Hair-Treating Compound |
|---|---|---|---|
| 61[1] | Citric (0.25%) | 9.58 | Silicone Blend (2%)[2] |
| 62[3] | Citric (0.33%) | 7.16 | Silicone Blend (2%) |
| 63 | Citric (0.48%) | 5.71 | Silicone Blend (2%) |
| 64 | Citric (0.96%) | 4.54 | Silicone Blend (2%) |
| 65 | Citric (1.44%) | 3.97 | Silicone Blend (2%) |
| 66 | Citric (1.92%) | 3.65 | Silicone Blend (2%) |
| 67 | Citric (0.45%) | 6.09 | Sulfur (elemental 2.03%, included in Carbopol-sulfur dispersion) |
| 68 | Citric (0.45%) | 5.81 | Zinc Pyrithione (2.1%) |
| 69 | Oleic (6.0%) | 5.97 | Silicone Blend (2%) |
| 70[4] | Oleic (3.5%) | 6.10 | Silicone Blend (2%) |
| 71[4] | Stearic (3.5%) | 5.80 | Silicone Blend (2%) |
| 72 | Palmitic[5] (1.0%) Citric (0.3%) | 5.80 | Silicone Blend (2.5%) |

[1]All compositions of Examples 61 through 71 included a total of 12.10% by weight anionic surfactants; and the compositions of Examples 61 through 69 included 3% by weight ADOGEN 240;
[2]Silicone blend including 33% 1 part by weight Silicone GUM SE-30 and 2 parts by weight SF 96-350 Silicone Fluid;
[3]Added 1% sodium chloride to increase viscosity;
[4]Composition included 1% by weight ADOGEN 240; and
[5]Composition included 16.2% by weight anionic surfactants, and 2.5% by weight dipalmityl amine.

The compositions of Examples 61 and 62 were water-thin liquids. Sodium chloride was added to the composition of Example 62 to increase the viscosity to 4850 cps. The compositions of Examples 61 and 62 were stable at room temperature, and at 120° F., for 4 weeks, exhibiting no phase separation. Therefore, it has been demonstrated that the present compositions suspend a water-insoluble hair treating compound by a mechanism other than thickening. The compositions of Examples 63–66 were stable at room temperature and at 120° F., showing no silicone separation after 4 weeks of storage. The compositions of Examples 67 and 68, each including a particulate antidandruff agent, demonstrated an excellent ability to suspend the particulate antidandruff agent with no separation or settling observed at room temperature, or at 120° F., after 2 weeks of storage.

The compositions of Examples 69 through 72 each utilized an aliphatic carboxylic acid including 16 or more carbon atoms, i.e., a fatty acid, to neutralize the secondary amine. Each composition was stable, exhibiting no silicone phase separation after 24 hours. The composition of Example 69 was a very thick, cream-like composition, whereas the compositions of Examples 70 and 71, each including only 1% by weight of the secondary amine, and the composition of Example 72, including 2.5% by weight of a secondary amine, were suspensions of low viscosity. Accordingly, a fatty acid including 16 or more carbon atoms is useful in neutralizing an amine of general structural formulas (I) or (II) or (III), which in turn effectively suspends a water-insoluble hair treating compound in a hair shampoo composition.

A fatty acid including more than about 16 carbon atoms provides a composition that often is too thick for consumer acceptance at the higher levels of amine, e.g., 3%, included in the composition. However, compositions having a consumer acceptable viscosity are provided when about 2.5% of the amine is included in the composition. A fatty acid including olefinic unsaturation, e.g., the oleic acid used in Examples 69 and 70, effectively neutralized the amine and suspended the water-insoluble hair treating compound, but provided a composition of decreased consumer acceptability because the resulting shampoo was too thick and demonstrated decreased composition esthetics. Therefore, in summary, to achieve the full advantage of the present invention in regard to balancing consumer esthetics with suspending ability, the aliphatic carboxylic acid utilized to neutralize the amine is a saturated acid, includes about 16 or fewer carbon atoms, and is used in a sufficient amount to suspend a water-insoluble hair-treating compound in a consumer-acceptable hair shampoo for at least the expected life of the hair shampoo.

To further demonstrate the ability of the suspending agent to provide a stable hair shampoo composition including a water-insoluble hair-treating compound, the following compositions of Examples 73 through 76 were prepared by the above-described method. The compositions of Examples 73 through 76 each include a water-insoluble antidandruff compound; the compositions of Examples 74 and 76 further include a water-insoluble silicone blend as a hair conditioner. Each composition of Examples 73 through 76 resisted phase separation and effectively delivered the water-insoluble hair treating compound, or compounds, to hair shampooed with the composition.

| Ingredient | EX. 73[1] | EX. 74 | EX. 75 | EX. 76 |
|---|---|---|---|---|
| Ammonium Lauryl Sulfate[2] | 3.75 | 3.75 | — | — |
| Sodium Lauryl Sulfate[3] | 6.75 | 6.75 | 10.5 | 10.5 |
| Ammonium Lauryl Ether Sulfate | 2.4 | 2.4 | 2.8 | 2.8 |
| Lauramide DEA | 1.05 | 1.05 | 1.23 | 1.23 |
| ADOGEN 240[4] | 3.50 | 3.50 | 3.00 | 3.00 |
| Citric Acid[5] | 0.50 | 0.50 | 0.50 | 0.50 |
| Sulfur[6] | 2.00[9] | 2.00[9] | — | — |
| Zinc complex of 2-pyridinethiol-1-oxide[7] | — | — | 1.05 | 1.05 |
| Silicone Blend[8] | — | 2.00 | — | 2.00 |
| Tetrasodium EDTA[9] | 0.08 | 0.08 | — | — |
| Dye | 0.001 | 0.001 | 0.002 | 0.002 |
| Fragrance | 0.35 | 0.35 | 0.35 | 0.35 |
| Preservative[10] | 0.15 | 0.15 | 0.15 | 0.15 |
| Ammonium Xylene Sulfonate | 0.15 | 0.15 | 0.18 | 0.18 |
| Soft water | q.s. | q.s. | q.s. | q.s. |
| Appearance: | pearlescent | pearlescent | pearlescent | pearlescent |

[1]Percent by weight of active ingredient in the composition;
[2]Added as a 30% by weight active solution;
[3]Added as a 30% by weight active solution;
[4]Di(hydrogenated tallow)amine, a secondary amine available from Sherex Chemical Co., Dublin, Ohio;
[5]Added as a 50% by weight aqueous solution;
[6]as elemental sulfur;
[7]ZINC OMADINE, available from Olin Corp., a 48% aqueous dispersion;
[8]Added as a 100% active blend including one part by weight Silicone GUM SE-30, a polydimethylsiloxane having a viscosity of about $15 \times 10^6$ to about $30 \times 10^6$ centipoises, and two parts by weight of Silicone Fluid 96-350, a polydimethylsiloxane having a viscosity of about 350 centipoises, both available from General Electric Silicone Products Division, Waterford, N.Y.;
[9]Added as a 39% aqueous solution of tetrasodium ethylenediaminetetraacetate; and
[10]DMDM hydantoin, methylisothiazolinone and methylchloroisothiazolinone.

Therefore, the method and composition of the present invention provide a shampoo composition that exhibits an exceptional ability to suspend either a liquid or a particulate water-insoluble hair treating compound, or a combination thereof. The increased ability to suspend the water-insoluble hair treating compound permits the incorporation of unexpectedly high amounts of silicones, hydrocarbons and other water-insoluble conditioning agents, or an antidandruff agent, or other hair-treating compound into a shampoo composition, or combination. It is both surprising and unexpected for an aqueous composition of the present invention, including a water-insoluble hair-treating compound, like a polydimethylsiloxane or an antidandruff agent, to effectively resist phase separation, to effectively cleanse the hair and to effectively deliver the hair treating compound to the hair or scalp, while maintaining an acceptable foam level and exhibiting sufficient physical and esthetic properties for consumer acceptance.

The following nonlimiting examples further demonstrate the shampoo compositions of the present invention.

EXAMPLE 77

| Ingredient | % by weight of active ingredient |
|---|---|
| Ammonium Lauryl Sulfate | 6.0 |
| Sodium Lauryl Sulfate | 4.5 |
| Ammonium Lauryl Ethyl Sulfate | 2.8 |
| Lauramide DEA | 1.25 |
| Palmitamidopropyl Dimethylamine | 3.0 |
| Citric Acid | 0.55 |
| Purcellin Oil | 2.0 |
| Optional Ingredients (dye, fragrance, preservatives, water softeners) | q.s. |

EXAMPLE 78

| Ingredient | % by weight of active ingredient |
|---|---|
| Ammonium Lauryl Sulfate | 11.0 |
| Ammonium Lauryl Ether Sulfate | 4.5 |
| Soya Diamine | 3.0 |
| Lauric Acid | 1.0 |
| Isopropyl Myristate | 2.0 |
| Optional Ingredients (dye, fragrance, preservatives, water softeners) | q.s. |
| Soft Water | q.s. to 100% |

EXAMPLE 79

| Ingredient | % by weight of active ingredient |
|---|---|
| Sodium Lauryl Sulfate | 15.0 |
| Lauramide DEA | 1.25 |
| Dipalmityl Amine | 2.0 |
| Lauric Acid | 1.0 |
| PERMETHYL 99A | 2.0 |
| Optional Ingredients (dye, fragrance, preservatives, water softeners) | q.s. |
| Soft Water | q.s. to 100% |

EXAMPLE 80

| Ingredient | % by weight of active ingredient |
|---|---|
| Ammonium Lauryl Sulfate | 9.0 |
| Ammonium Lauryl Ether Sulfate | 1.2 |
| Sodium Lauryl Sulfate | 6.0 |
| Lauramide DEA | 0.5 |
| Dipalmityl Amine | 2.5 |
| Palmitic Acid | 1.0 |
| Citric Acid | 0.3 |
| Silicone Blend | 2.5 |
| Hydroxypropyl Methylcellulose | 0.2 |
| Optional Ingredients (dye, fragrance, preservatives, water softeners) | q.s. |
| Soft Water | q.s. to 100% |

EXAMPLE 81

| Ingredient | % by weight of active ingredient |
|---|---|
| Ammonium Lauryl Sulfate | 3.75 |
| Sodium Lauryl Sulfate | 6.75 |
| Ammonium Lauryl Ether Sulfate | 2.4 |
| Lauramide DEA | 1.0 |
| Dipalmityl Amine | 3.0 |
| Citric Acid | 0.5 |
| Selenium Sulfide | 2.0 |
| Silicone Blend | 2.0 |
| Optional Ingredients (dye, fragrance, preservatives, water softeners) | q.s. |
| Soft Water | q.s. to 100% |

EXAMPLE 82

| Ingredient | % by weight of active ingredient |
|---|---|
| Sodium Lauryl Sulfate | 10.0 |
| Ammonium Lauryl Ether Sulfate | 3.0 |
| Lauramide DEA | 1.25 |
| Stearamidopropyl Dimethylamine | 3.5 |
| Palmitic Acid | 1.5 |
| Undecylenic Acid | 1.5 |
| Optional Ingredients (dye, fragrance, preservatives, water softeners) | q.s. |
| Soft Water | q.s. to 100% |

EXAMPLE 83

| Ingredient | % by weight of active ingredient |
|---|---|
| Ammonium Lauryl Sulfate | 8.0 |
| Sodium Lauryl Sulfate | 6.75 |
| Ammonium Lauryl Ether Sulfate | 1.6 |
| Lauramide DEA | 0.7 |
| Dipalmityl Amine | 3.5 |
| Palmitic Acid | 1.2 |
| Citric Acid | 0.58 |
| Sulfur Slurry | 2.03 |
| Zinc Oxide | 0.025 |
| Silicone Blend | 2.0 |
| Hydroxypropyl Methylcellulose | 0.15 |
| Optional Ingredients (dye, fragrance, preservatives, water softeners) | q.s. |
| Soft Water | q.s. to 100% |

EXAMPLE 84

| Ingredient | % by weight of active ingredient |
|---|---|
| Ammonium Lauryl Sulfate | 9.0 |
| Sodium Lauryl Sulfate | 7.5 |
| Ammonium Lauryl Ether Sulfate | 2.4 |
| Lauramide DEA | 1.05 |
| Dipalmityl Amine | 3.5 |
| Palmitic Acid | 1.5 |
| Sulfur Slurry | 2.0 |
| Zinc Oxide | 0.025 |
| Hydroxypropyl Methylcellulose | 0.20 |
| Optional Ingredients (dye, fragrance, preservatives, water softeners) | q.s. |
| Soft Water | q.s. to 100% |

Obviously, many modifications and variations of the invention as hereinbefore set forth can be made without departing from the spirit and scope thereof, and therefore only such limitations should be imposed as are indicated by the appended claims.

We claim:

1. A homogeneous shampoo-conditioner composition comprising:
   (a) about 3% to about 40% by weight of an anionic cleansing surfactant;
   (b) about 0.1% to about 10% by weight of a water-insoluble conditioning agent;
   (c) a suspending agent comprising:
      (i) from about 1% to about 10% by weight of the composition of an amine having the general structural formula

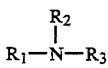

wherein $R_1$ is an alkyl group including at least 16 carbon atoms; $R_2$ is selected from the group consisting of hydrogen, an alkyl group having one to about 22 carbon atoms, benzyl and phenyl; and $R_3$ is selected from the group consisting of hydrogen, methyl, benzyl and phenyl, wherein said amine has a water solubility of 0.5 grams or less per 100 milliliters of water, and wherein said amine is a solid compound at room temperature; and (ii) a sufficient amount of an acid such that essentially no solid particles of the amine are present in the composition, said acid selected from the group consisting of an inorganic mineral acid, an aliphatic carboxylic acid including up to about 22 carbon atoms, an aromatic carboxylic acid, and combinations thereof; and (d) an aqueous carrier.

2. The composition of claim 1, wherein the conditioning agent is selected from the group consisting of a silicone conditioning agent, a hydrocarbon conditioning agent, a water-insoluble fatty alcohol having about 12 to about 22 carbon atoms, a water-insoluble fatty ester having about 9 to about 34 carbon atoms, and combinations thereof.

3. The composition of claim 2, wherein the silicone conditioning agent is a nonvolatile silicone conditioning agent, a volatile silicone conditioning agent, or a combination thereof.

4. The composition of claim 2, wherein the hydrocarbon conditioning agent is a volatile hydrocarbon conditioning compound.

5. The composition of claim 1, wherein the conditioning agent is selected from the group consisting of a polysiloxane polyether copolymer; an acetylated lanolin alcohol; a lanolin-derived extract of sterol, a sterol ester; lanolin alcohol concentrate; an isopropyl ester of a lanolin fatty acid; a polyol fatty acid; a keratin protein derivative; an amino-functional silicone; a mineral oil and lanolin alcohol mixture; a high molecular weight ester of lanolin; a vinylpyrrolidone/dimethylaminoethylmethacrylate copolymer; a 5 mole ethylene oxide adduct of soya sterol; a 10 mole ethylene oxide adduct of soya sterol; a stearic acid ester of an ethoxylated methyl glucoside; a hydroxylated lanolin; lactamide MEA; stearamide MEA; an ethoxylated long chain alcohol; a propoxylated long chain alcohol; hydrolyzed animal keratin; ethyl hydrolyzed animal keratin; avocado oil; sweet almond oil; grape seed oil; jojoba oil; apricot kernel oil; sesame oil; hybrid safflower oil; wheat germ oil; an ethyl ester of a hydrolyzed animal protein; a blend of cetyl and stearyl cetearyl alcohol with an ethoxylated cetyl or stearyl alcohol; a propoxylated (1-10 moles) lanolin alcohol; isostearamide DEA; a hydrolyzed collagen protein; and combinations thereof.

6. The composition of claim 1, wherein the water-insoluble conditioning agent is present in an amount of about 0.5% to about 5% by weight of the composition.

7. The composition of claim 1, wherein the amine is a solid compound at room temperature and has a water solubility of 0.5 grams or less per 100 milliliters of water.

8. The composition of claim 1, wherein the amine is present in an amount of about 1.5% to about 5% by weight of the composition.

9. The composition of claim 1, wherein the amine is selected from the group consisting of $C_{20-22}$ amine, hydrogenated tallow amine, stearyl amine, tallow amine, hexadecylamine, octadecylamine, di(hydrogenated tallow)amine, dipalmityl amine, di(hydrogenated tallow) methylamine, distearyl methyl amine, methyl dibehenamine, and combinations thereof.

10. The composition of claim 1, wherein the inorganic mineral acid is selected from the group consisting of hydrochloric acid, sulfuric acid, nitric acid, phosphoric acid, and combinations thereof.

11. The composition of claim 1 wherein the aliphatic carboxylic acid is selected from the group consisting of acetic acid, lactic acid, citric acid, tartaric acid, propionic acid, butyric acid, pentanoic acid, glycolic acid, decanoic acid, lauric acid, palmitic acid, octanoic acid, oleic acid, stearic acid, and combinations thereof.

12. The composition of claim 1, wherein the aliphatic carboxylic acid is a saturated aliphatic acid including about 16 carbon atoms or less.

13. The composition of claim 1, wherein the aromatic carboxylic acid is selected from the group consisting of benzoic acid, salicylic acid, phthalic acid, isophthalic acid, terephthalic acid, toluic acid, and combinations thereof.

14. The composition of claim 1 having a pH of about 3 to about 8.

15. The composition of claim 1 further comprising 0% to about 5% of a nonaqueous solvent.

16. The composition of claim 1, wherein the anionic cleansing surfactant is an alkyl sulfate, an alkyl ether sulfate or a combination thereof; the water-insoluble conditioning agent is a polydimethylsiloxane, a volatile hydrocarbon, or a combination thereof; the amine is hydrogenated tallow amine, di(hydrogenated tallow)amine, dipalmityl amine, distearyl amine, distearyl methyl amine or a combination thereof; and the acid is citric acid, lactic acid, phosphoric acid, hydrochloric acid, palmitic acid, lauric acid or a combination thereof.

17. The composition of claim 1 further comprising 0% to about 5% by weight of a nonionic surfactant.

18. The composition of claim 16, wherein the nonionic surfactant is an alkanolamide.

19. The composition of claim 1 comprising:
(a) about 10% to about 25% by weight of an anionic cleansing surfactant;
(b) about 0.5% to about 5% by weight of a water-insoluble conditioning agent;
(c) a suspending agent comprising:
  (i) about 1.5% to about 5% by weight of dipalmityl amine; and
  (ii) a sufficient amount of citric acid, palmitic acid or a combination thereof such that no particles of the dipalmityl amine are present in the composition; and
(d) an aqueous carrier.

20. The composition of claim 19 wherein the water-insoluble conditioning agent is a nonvolatile silicone conditioning agent, a volatile silicone conditioning agent or a combination thereof.

21. A homogeneous shampoo-conditioner composition comprising:
(a) about 3% to about 40% by weight of an anionic cleansing surfactant;

(b) about 0.1% to about 10% by weight of a water-insoluble conditioning agent;
(c) a suspending agent comprising:
(i) from about 1% to about 10% by weight of the composition of an amine having the general structural formula

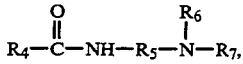

wherein $R_4$ is an alkyl group having at least 13 carbon atoms; $R_5$ is an alkylene moiety having one to four carbon atoms; and $R_6$ and $R_7$ are, independently, an alkyl group having one to four carbon atoms, wherein said amine has a water solubility of 0.5 grams or less per 100 milliliters of water, and wherein said amine is a solid compound at room temperature; and
(ii) a sufficient amount of an acid such that essentially no solid particles of the amine are present in the composition, said acid selected from the group consisting of an inorganic mineral acid, an aliphatic carboxylic acid including up to about 22 carbon atoms, an aromatic carboxylic acid, and combinations thereof; and
(d) an aqueous carrier.

22. The composition of claim 21 wherein the amine is selected from the group consisting of stearamidopropyl diethylamine, stearamidoethyl diethylamine, stearamidoethyl dimethylamine, palmitamidopropyl dimethylamine, behenamidopropyl dimethylamine, myristamidopropyl dimethylamine, stearamidopropyl dimethylamine, and combinations thereof.

23. A homogeneous shampoo-conditioner composition comprising:

(a) about 3% to about 40% by weight of an anionic cleansing surfactant;
(b) about 0.1% to about 10% by weight of a water-insoluble conditioning agent;
(c) a suspending agent comprising:
(i) from about 1% to about 10% by weight of the composition of an amine having the general structural formula

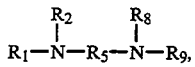

wherein $R_1$ is an alkyl group including at least 16 carbon atoms; $R_2$ is selected from the group consisting of hydrogen, an alkyl group having one to about 22 carbon atoms, benzyl and phenyl; $R_5$ is an alkylene moiety having one to four carbon atoms; and $R_8$ and $R_9$ are, independently, hydrogen or an alkyl group having 1 to 4 carbon atoms, wherein said amine has a water solubility of 0.5 grams or less per 100 milliliters of water, and wherein said amine is a solid compound at room temperature; and
(ii) a sufficient amount of an acid such that essentially no solid particles of the amine are present in the composition, said acid selected from the group consisting of an inorganic mineral acid, an aliphatic carboxylic acid including up to about 22 carbon atoms, an aromatic carboxylic acid, and combinations thereof; and
(d) an aqueous carrier.

24. The composition of claim 23 wherein the amine is selected from the group consisting of hydrogenated tallow diamine, tallow diamine and a combination thereof.

* * * * *

UNITED STATES PATENT AND TRADEMARK OFFICE
CERTIFICATE OF CORRECTION

PATENT NO. : 5,393,519

DATED : February 28, 1995

INVENTOR(S) : TERESA J. DOWELL ET AL.

It is certified that error appears in the above-identified patent and that said Letters Patent is hereby corrected as shown below:

Column 12, line 56, "cocohate" should be --coconate--

Signed and Sealed this

Sixth Day of June, 1995

Attest:

BRUCE LEHMAN

Attesting Officer     Commissioner of Patents and Trademarks